United States Patent [19]

Tunick et al.

[11] 4,316,877
[45] Feb. 23, 1982

[54] EXTRACTION OF URANIUM VALUES FROM PHOSPHORIC ACID

[75] Inventors: Allen A. Tunick, Boonton; Theodore Largman, Morristown; Stylianos Sifniades, Madison, all of N.J.

[73] Assignee: Allied Corporation, Morris Township, Morris County, N.J.

[21] Appl. No.: 96,853

[22] Filed: Nov. 23, 1979

[51] Int. Cl.$^3$ ............... C01G 43/00; C01B 25/238
[52] U.S. Cl. ........................ 423/10; 260/502.4 A
[58] Field of Search ............... 423/10; 260/502.4 A

[56] References Cited

U.S. PATENT DOCUMENTS

| | | | |
|---|---|---|---|
| 2,859,094 | 11/1958 | Schmitt et al. | 423/10 |
| 2,937,925 | 5/1960 | Blake et al. | 423/10 |
| 3,558,300 | 1/1971 | Wagner | 71/34 |
| 3,711,591 | 1/1973 | Hurst et al. | 423/10 |
| 3,835,214 | 9/1974 | Hurst et al. | 423/10 |
| 3,855,284 | 12/1974 | Germscheid | 260/502.4 A |

OTHER PUBLICATIONS

Greek et al., "Uranium Recovery from Wet Process Phosphoric Acid" *Ind. and Eng. Chem.*, vol. 49, p. 628 (1957).
Kabachnik et al., "Organophosphorus Complexones" *Russian Chem. Reviews*, 43(9) (1974) p. 733.
Kabachnik et al., "Complex Forming Properties of HEDPA in Aqueous Soln." *Proc. Acad. Sci. USSR* 177 p. 582 (1967).

*Primary Examiner*—Deborah L. Kyle
*Attorney, Agent, or Firm*—Alan M. Doernberg; Gerhard H. Fuchs; Richard C. Stewart, II

[57] ABSTRACT

Aqueous phosphoric acid solutions containing uranium values are contacted with an organic solution of a mixture of organophosphorus compounds produced from a carboxylic acid and PCl$_3$ in the presence of water or from corresponding acid halides or anhydrides and phosphorous acid to extract the uranium values. The organophorus compounds generally include an alkane-1,1,2-triphosphonic acid or a 1-hydroxy-1,1-alkanediphosphonic acid or both, which differ from common organophosphorus extractants in having a carbon-phosphorus bond. The extraction has high distribution coefficients even when the phosphoric acid solution is 10 molar or more and even when the extraction is conducted at elevated temperatures such as 60° C. While distribution coefficients in the presence of iron are higher for tetravalent uranium, efficient extraction can be conducted of hexavalent uranium as well. Uranium values are recovered from the organic solution by contacting it with about 40–70 weight percent aqueous HF and separating a uranium-rich precipitate from the solution.

27 Claims, No Drawings

EXTRACTION OF URANIUM VALUES FROM PHOSPHORIC ACID

DESCRIPTION

Background of the Invention

The present invention relates to the extraction of uranium values from aqueous phosphoric acid solutions with organic solutions containing organophosphorus extractants.

Organic solutions of dialkylphosphoric acids such as di-2-ethylhexylphosphoric acid (D2EHPA) with trialkylphosphine oxides such as trioctylphosphine oxide (TOPO) as synergists are used to extract hexavalent uranium from phosphoric acid solutions. Uranium values are recovered from such organic solutions by reduction to tetravalent uranium and stripping with more concentrated phosphoric acid.

Organic solutions of mono- and di-alkylphenyl esters of phosphoric acid such as mono- and di-octylphenyl-phosphoric acid (OPPA) are used to extract tetravalent uranium from phosphoric acid solutions. Uranium values are recovered by oxidation to hexavalent uranium and stripping with more concentrated phosphoric acid.

A process has been described for extracting tetravalent uranium from phosphoric acid with organic solutions of pyrophosphate esters and stripping by precipitation with aqueous $HF\text{-}H_2SO_4$ solutions.

The organophosphorus compounds used in these various processes can be represented by the following formulae with R representing hydrocarbon substituents such as alkyl:

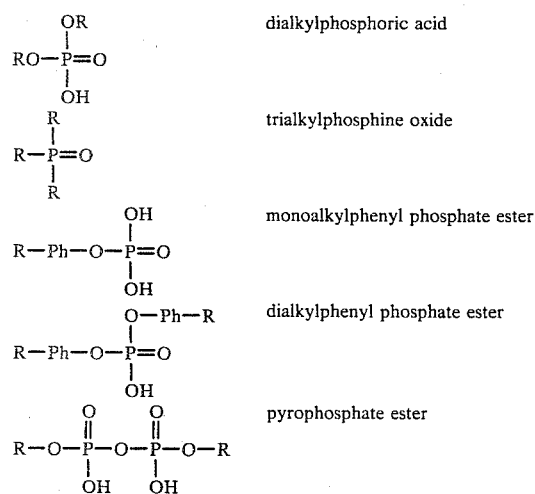

While extraction of uranium values is accomplished with any of these three systems, the distribution coefficient (ratio between concentration of uranium in the organic solution and concentration of uranium in the phosphoric acid solution with which it is in contact at equilibrium) declines to unacceptable levels when either the temperature is above about 40° C. or the concentration of phosphoric acid is above about 8 molar or both. In addition, both the D2EPHA-TOPO process and the OPPA process require oxidative or reductive treatment of the phosphoric acid prior to extraction in order to convert the uranium values to the appropriate oxidation state, as well as reduction or oxidation in conjunction with stripping the loaded organic phases. Because of the interference by other cations and especially ferric ions, the concentration of OPPA in the organic solution is limited to below levels where iron-OPPA precipitates form during extraction. Processes employing pyrophosphate esters not only require prior reductive treatment, but also have the additional disadvantage of loss of extraction efficiency due to hydrolytic instability of the pyrophosphate esters.

In order to compensate for the limited extractive power of the prior art organophosphorus extraction agents, limitations must be placed on the process to avoid excessively high inventories of organic solution or a large number of extraction stages. First, wet process phosphoric acid must be used at conventional concentrations of 5–7 molar. More concentrated acid such as 8–11 molar or higher, as is produced by processes such as the energy conserving hemihydrate process, complexes the uranium values too well and is difficult to use with conventional extractants. Furthermore, fresh wet process acid, normally at 50°–70° C., must be cooled to about 40° C. or lower before contacting with solutions of conventional extractants in order to achieve favorable equilibria. This cooling requires additional equipment and energy since the acid is usually reheated after extraction for further concentration.

BRIEF SUMMARY OF THE INVENTION

The present invention includes a process for recovering uranium values from an aqueous phosphoric acid solution by extracting the uranium values from the aqueous phosphoric acid solution with an organic solution containing an organophosphorus extractant and stripping the uranium values from the organic solution wherein the improvement comprises:

(a) contacting the aqueous phosphoric acid solution with an organic solution of the organophosphorus extractant to extract uranium values into the organic solution, (b) contacting the organic solution containing uranium values with an aqueous hydrogen fluoride solution of between about 30 and about 70 weight percent hydrogen fluoride, and (c) recovering the uranium values as a precipitate.

The organophosphorus extractants used in the present invention may be prepared by either:

(1) reaction of the acid R-COOH with $PCl_3$ in the presence of water, or (2) reaction of the acid halide R-COCl or the anhydride

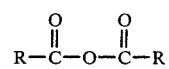

with phosphorous acid.

Thus the organophosphorus extractant useful in the present invention can be defined as either:

(a) the reaction product of the acid R-COOH with $PCl_3$ in the presence of water, or (b) the reaction product of the acid halide R-(COCl) or the anhydride

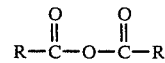

with phosphorous acid, or (c) a mixture of organophosphorus compounds containing an alkane-1,1,2-triphosphonic acid of the formula R'CH(PO₃H₂)CH(PO₃H₂)₂ or a 1-hydroxy-1,1-diphosphonic acid of the formula RC(OH)(PO₃H₂)₂ or both, where R is alkyl of 8–18 carbons and R' is alkyl of 7–17 carbons.

The reaction mixture of the above reactions can be subjected to distillation under reduced pressure in order to remove volatile organics and HCl by-product (if present). One suitable purification method is to heat with a lower alkanol before distillation to convert the acid R-COOH to an ester which is more volatile. The distillation residue is a mixture of organophosphorus compounds that is capable of strongly chelating uranium. One of the components of the mixture when the reaction is completed at high temperatures (e.g. 150° C.) is an alkane-1,1,2-triphosphonic acid of structure R'CH(PO₃H₂) CH(PO₃H₂)₂ where R' is an alkyl group containing one less carbon atom than the R group of the starting R-COOH. The triphosphonic acid can be removed by extensive extraction with water; however, the remaining mixture of organophosphorus compounds can still chelate uranium strongly.

U.S. Pat. No. 3,855,784, issued to H. G. Germscheid, describes a method for the synthesis of 1-hydroxy-1,1-diphosphonic acids of structure RC(OH)—(PO₃H₂)₂ from carboxylic acids R-COOH by reaction with PCl₃ and water. Examples 7–10 of that patent describe such methods specifically with six, seven, sixteen and eighteen carbon aliphatic acids; and the patent represents the products to be 1-hydroxy-1,1-alkanediphosphonic acids even when the reaction is conducted at 140°–160° C. as in these Examples. It has been found that the product actually is a mixture of organophosphorus compounds, containing as a principal component a 1,1,2-alkanetriphosphonic acid, and not containing the 1-hydroxy-1,1-alkanediphosphonic acid in any significant amount. It has also been found that, for use as an extractant as in the present invention, the preferred products are obtained when using organic acids of 9–15 carbons such as nonanoic acid or dodecanoic acid as a reactant rather than acids of 7 or 16 carbons.

At higher temperatures (e.g. 150° C.) 1-hydroxy-1,1-diphosphonic acids are not formed to any significant degree, but other organophosphorus compounds such as the above triphosphonic acids are formed. Both classes of phosphonic acids are active extractants for uranium according to the present process. Thus the present invention includes organophosphorus compounds prepared by the above process at high or low temperature and the use thereof for uranium extraction, and also includes using mixtures of organophosphorus compounds including 1,1,2-triphosphonic acids or 1-hydroxy-1,1-diphosphonic acids, or both, for uranium extraction.

Thus, it will be appreciated that the novel extractants of this invention which are used in the method of this invention can be mixtures of several uranium chelating organophosphorus compounds, one of which is either a triphosphonic acid or a 1-hydroxy-1,1-diphosphonic acid or both, and may also contain several additional organophosphorus compounds as well as impurities. In order to be used for uranium extraction, these extractants are dissolved in a suitable water-immiscible solvent, preferably containing other organophosphorus compounds as cosolvent as described below.

We have found that organic solutions of such compounds, where R is an alkyl group from eight to eighteen carbon atoms, or R' is an alkyl group of seven to seventeen carbons atoms, extract uranium as either U(IV) or U(VI) from phosphoric acid solutions of concentration up to 15 M. Preferred are the novel compounds of 9–15 carbons such as those formed from nonanoic or dodecanoic acids. We have further found that the uranium can be recovered from the extract by stripping with aqueous hydrogen fluoride of 30–70 wt % concentration. The bulk of the stripped uranium precipitates as crude uranium fluoride and is separated from the aqueous phase by centrifugation, filtration or other means.

DETAILED DESCRIPTION OF THE INVENTION

The main advantage of the process of our invention is that it is applicable to the recovery of uranium from phosphoric acid streams of relatively high concentration, such as 8–11 M, such as are provided by the energy conserving hemihydrate process. Another advantage is the fact that the process can operate close to the temperature (60°–70° C.) at which wet process phosphoric acid streams are normally available at the plant, thus obviating the necessity for extensive cooling facilities. The existing processes are applicable only to less concentrated (about 7 molar or less) phosphoric acids and require cooling to about 40° C. because the distribution coefficient of uranium between phosphoric acid and extractant is unfavorable at higher temperatures. A further advantage is that prior oxidation or reduction of the uranium containing phosphoric acid is not necessary, although reduction is helpful because it reduces the concentration of ferric ion which interferes with the extraction to some extent.

The concentration of the phosphoric acid used is not itself critical, with concentrations of as low as about 5 or as high as about 15 molar being suitable. The increased extraction power of the present extractants makes the invention particularly applicable to more concentrated acids of 8 molar or higher, such as about 8 to about 11 molar. Conventional extractants have limited effectiveness in extracting uranium from such concentrated acid. Excessive amounts of suspended solids in the acid are detrimental to the process. These may be removed by conventional means, such as filtration, flocculation, etc.

In the above formula, R (as present in the acid, acid halide or acid anhydride used to form the hydroxydiphosphonic or triphosphonic acid) may be linear or branched alkyl and may have 8 to 18 carbons, preferably 9–15 carbons. Shorter alkyl chains result in extractants that become too soluble in the aqueous solutions with which the organic solution comes in contact. Longer alkyl chains result in reduced extraction power.

The precise temperature at which the aqueous phosphoric acid is contacted by the organic solution is not critical, with about 0° C. to about 75° C. being a suitable general range. Temperatures of about 50° C. to about 70° C. are preferred since fresh acid can be contacted at such temperatures without substantial cooling. It should be appreciated that increased extractive power of the present extractants compared to the extractant power of prior art extractants is significant in making possible such higher temperature operation.

The organic solution may contain any conventional organic solvent or solvent-cosolvent system in which the extractants are soluble and which solvent or solvent and cosolvent are substantially insoluble in the phosphoric acid. Organic solvent or cosolvents dissolving to a greater extent than 0.1 g/L in the phosphoric acid under extraction conditions are undesirable because of excessive solvent losses during operation. Exemplary solvents include hydrocarbons such as kerosene and xylenes and other organics such as chlorinated hydrocarbons. When the extractants have limited solubility in the organic, as may be the case especially when the R group is at the lower end of the above ranges, a cosolvent may be used to increase their solubility. Especially for hydrocarbons such as kerosene as solvent, the trialkyl phosphate esters and the dialkyl alkylphosphonate esters are especially good cosolvents, with the latter being preferred.

The concentration of the extractants in the organic solution is not critical; a range of about 5 to 25 weight percent is suitable, with the lower end of the range being controlled by considerations of extraction power and required total inventory of organic solution, while the upper end is controlled by the solubility of the extractant and the rate of increase in extraction strength at higher levels of extractant. A preferred range is about 7 to about 15 weight percent.

The volume ratio of phosphoric acid solution to organic solution used is not critical, but is generally a matter of choice based upon engineering considerations. A suitable preferred range is between about 10:1 and about 1:5, with higher or lower ratios also being suitable.

Because of the great extractant strength of the organic solutions used in the present invention, stripping by conventional techniques including even precipitation with 15–20% HF and 20–25% $H_2SO_4$ in water as described in B. F. Greek et al., *Industrial and Engineering Chemistry*, vol. 49, p. 638 (1957) is ineffective. Aqueous HF solutions of about 40–70% are required. Superatmospheric pressure is applied if necessary to prevent vaporization of HF.

EXAMPLE 1

Preparation of $C_9$-Extractant From Nonanoic Acid

Nonanoic acid, 79.1 g, and water, 9.0 g, were mixed well and to the mixture was added dropwise phosphorus trichloride, 45.7 g. The rate of addition was limited by the copious hydrogen chloride evolution. The mixture was stirred and maintained at about 50° C. during the addition and then was heated at 150° C. for five hours. After cooling, absolute ethanol, 35 mL, was added and the resulting solution was subjected to distillation under reduced pressure using a 15 cm Vigreaux column until a pot temperature of 140° C. was reached at about 1 mm Hg pressure. The residue, hereinafter called "C-9 extractant", was a very viscous resin practically insoluble in hydrocarbons, but soluble in acetone or chloroform. Similar product was obtained when water, instead of ethanol, was added to the reaction mixture prior to distillation under vacuum.

Analysis by thin layer chromatography on silica gel plates using methanol/concentrated ammonia (98:2 v/v) as eluent showed the presence of five or six separate components in the crude product. One of the components was isolated by repeated extraction of a chloroform solution of the crude product with water. Upon evaporation of the aqueous extracts, a white crystalline material was obtained in 30 wt. % yield, based on crude product. After purification by dissolution in acetone and precipitation with chloroform, the material was examined by $^1H$, $^{13}C$ and $^{31}P$ NMR, elemental analysis and potentiometric titration and was assigned the structure nonane-1,1,2-triphosphonic acid, which is a new composition of matter.

Although nonane-1,1,2-triphosphonic acid is very soluble in water and essentially insoluble in chloroform and hydrocarbon solvents, a solution of crude $C_9$-extractant (10 wt %) in dibutyl butylphosphonate (10 wt %) and kerosene (80 wt %) can be used repeatedly for extraction of uranium from phosphoric acid without excessive loss of organic material to the acid. Thus when such a solution was shaken with equal volumes of 10 M phosphoric acid, the total concentration of carbon in the phosphoric acid was 0.11 g per 100 mL.

When the reaction of nonanoic acid, water and phosphorus trichloride was carried out at 110° C. for 16 hours, 70% of the crude product obtained after addition of water and evaporation of volatiles under vacuum was soluble in water and consisted essentially of 1-hydroxy-1,1-nonanediphosphonic acid with only a minor amount of nonane-1,1,2-triphosphonic acid. The structure assignment of 1-hydroxy-1,1-nonanediphosphonic acid was made on the basis of $^{13}C$ and $^{31}P$ NMR spectra. Examination by NMR of the crude $C_9$-extractant obtained by reaction at 150° C. indicated that 1-hydroxy-1,1-nonanediphosphonic acid was not present in detectable amounts in that product.

In similar manner $C_9$, $C_{12}$, $C_{16}$ and $C_{18}$ extractants were prepared at 150° C. from iso-nonanoic, lauric, iso-hexadecanoic and stearic acids respectively. NMR analysis of the $C_{12}$ extractant revealed that dodecane-1,1,2-triphosphonic acid was a major component of the crude product and that 1-hydroxy-1,1-dodecane diphosphonic acid was absent. When a solution of the crude $C_{12}$ extractant (10 wt %) in dibutyl butylphosphonate (10 wt %) and kerosene (80 wt %) was shaken with equal volume of 10 M phosphoric acid, the total carbon in the phosphoric acid was 0.01%. The same amount of carbon was found when a 10 wt % kerosene solution of dibutyl butyl phosphonate was used instead. These results indicate that loss of material from the crude $C_{12}$ extractant during contact with phosphoric acid is negligible. A $C_{12}$ extractant was also made from lauric acid by reaction at 110° C. for 16 h. The main component of this acid extractant was 1-hydroxy-1,1-dodecanediphosphonic acid.

EXAMPLE 2

Uranium Extraction with Crude $C_9$-Extractant/Chloroform

An extractant solution was prepared by dissolving 5.5 g of the crude $C_9$-product of Example 1 in 54 mL chloroform. Aliquots of this solution were shaken well at room temperature for 1 min. with equal volumes of uranium-containing phosphoric acid samples and the aqueous layers were analyzed for uranium and compared to the original values. The results are shown in Table I. Runs A and B demonstrate the extractive power of the extractant in chloroform for either U(IV) or U(VI) from pure concentrated phosphoric acid. Runs C and D demonstrate the high extraction power of this system using two samples of crude phosphoric acid of about 6 M concentration, produced at the Geismar plant of Allied Chemical Corporation, that had previously been reduced. Runs E and F demonstrate that the extractive power was diminished, but was still of practical value, when the above 6 M phosphoric acid was either used without prior treatment or oxidized by the addition of hydrogen peroxide. Run G shows that even concentrated crude acid could be used for extraction, although the distribution coefficient was rather low in this case.

TABLE I

Extraction of Uranium by C$_9$-Extractant/Chloroform[a]

| Run | Oxidation State of U | Phosphoric Acid Concentration | U Concentration mg/L Before | U Concentration mg/L After | Distribution Coefficient[b] |
|---|---|---|---|---|---|
| A | U(IV) | ~15M/Reagent | 66.9 | 9.1 | 6.3 |
| B | U(VI) | ~15M/Reagent | 64.0 | 9.1 | 5.9 |
| C | U(IV) | ~6M/Reduced | 119.8 | 1.2 | 99.0 |
| D | U(IV) | ~6M/Reduced | 119.6 | 0.9 | 132.0 |
| E | U(IV+VI) | ~6M/Untreated | 120.3 | 17.8 | 5.8 |
| F | U(VI) | ~6M/Oxidized | 123.4 | 26.0 | 3.7 |
| G | U(IV+VI) | 12.9M/Untreated | 224.5 | 131.5 | 0.7 |

[a] A 10 wt/v % solution was used, in equal volume to the phosphoric acid sample.
[b] Defined as the ratio of concentrations of uranium in the organic phase and the phosphoric acid, respectively.

EXAMPLE 3

Extraction/Stripping Cycle

An extractant solution containing 10% crude C$_9$-extractant, 40% tributylvphosphate and 50% kerosene (by weight) was prepared. A 25 g (29 mL) aliquot of this solution was stirred for 2 h at room temperature with 500 mL of 5.6 M wet process phosphoric acid produced at the Geismar plant of Allied Chemical Corporation. This acid had been previously subjected to reduction and was known to contain 106.5 mg/L uranium and 5.5 g/kg Fe(II). After extraction, the phosphoric acid was analyzed and found to contain 10.5 mg/L uranium. This result corresponded to a distribution coefficient of 157. The extractant, 26.4 mL, was next stirred for 1 h at room temperature with 25 g of 48% aqueous hydrogen fluoride and the aqueous layer was separated and centrifuged. A green precipitate was obtained that weighed 123.2 mg after drying at 100° C. under reduced pressure and contained 37.3 mg uranium. When corrected for sampling losses (1 mL of extractant and 1 mL of aqueous strip solution) the prorated quantity of uranium produced was 40.3 mg.

To the stripped organic layer was added a 2 g aliquot of fresh extractant solution and the mixture was stirred as described above with another 500 mL aliquot of the same wet process phosphoric acid. After extraction, the acid contained 29 mg/L uranium. The extractant, 22.3 g, was next stripped with the aqueous hydrogen fluoride solution from the previous stripping operation, augmented by 3 g of fresh 48% aqueous hydrogen fluoride. A green precipitate was obtained by centrifuging the aqueous layer. This sequence of extraction/stripping/centrifuging was repeated a total of six times, each time adding small amounts of fresh extractant solution and 48% hydrogen fluoride, respectively, to the recycled extractant and stripping solution in order to make up for sampling and mechanical losses. The results are summarized in Table II.

TABLE II

Uranium Extraction/Stripping

| Cycle | Temp. °C. | Solutions Added Extractant | Solutions Added 48% HF | Precipitate mg | U Recovered, mg Actual | U Recovered, mg Corrected |
|---|---|---|---|---|---|---|
| 1 | 22 | 25 | 25 | 123.2 | 37.3 | 40.3 |
| 2 | 22 | 2 | 3 | 157.3 | 43 | 45 |
| 3 | 22 | 4 | 2 | 88.1 | 24.5 | 25.7 |
| 4 | 50 | 3 | 3.4 | 100.0 | 27 | 28 |
| 5 | 50 | 7.7 | 3 | 123.6 | 22.6 | 25.3 |
| 6 | 50 | 4 | — | 87.5 | 28.9 | 32.8 |

EXAMPLE 4

Extraction by Crude C$_9$-Extractant/DBBP/Kerosene

Crude C$_9$-extractant, 5 g, was mixed with dibutylvbutylphosphonate (DBBP), 5 g, then kerosene, 40 g, was added. A 5 mL aliquot of crude Geismar phosphoric acid, 5.6 M, which contained uranium, 106 mg/L was shaken at 25° C. with 2.5 mL of the extractant solution. After extraction, the uranium content of the acid was 30 mg/L, corresponding to a distribution coefficient of 5.1. A similar experiment was performed with crude phosphoric acid, 8.13 M, produced by the Tennessee Valley Authority (TVA) using the hemihydrate process. This acid contained uranium, 96.5 mg/L. After extraction the uranium content was 19.4 mg/L, corresponding to a distribution coefficient of 7.9. When the experiments were repeated at 60° C., the distribution coefficients were 3.0 and 4.1, respectively, with the Geismar and TVA acids. Experiments were conducted in similar fashion with other phosphoric acid samples. These results are summarized in Table III. The acids extracted in experiments A-D and F were Geismar samples. The acids extracted in Examples E and G were TVA samples.

TABLE III

| Run | Acid Molarity | Reduction | Extraction Temperature °C. | Distribution Coefficient |
|---|---|---|---|---|
| A | 5.6 | Yes | 23 | 56 |
| B | 7.8 | Yes | 23 | 24 |
| C | 10.7 | Yes | 23 | 12 |
| D | 5.6 | Yes | 60 | 23 |
| E | 8.1 | Yes | 60 | 50 |
| F | 5.6 | No | 60 | 3 |
| G | 8.1 | No | 60 | 4 |

These results show good extraction, even at 60° C., with unreduced acid and exceptional extraction of reduced acid. Because the acid was not fresh, it is likely that the unreduced acid contained a higher proportion of trivalent iron than fresh acid because of oxidation by air. Fresh acid would therefore be expected to produce better results than are reported in Runs F and G.

EXAMPLE 5

Comparison of Crude C$_9$-Extractant with Water-washed C$_9$-Extractant

The crude C$_9$-extractant solution of Example 4 was used to extract uranium from untreated 8.13 M TVA acid at 50° C., and a distribution coefficient of 3.9 was obtained. The distribution coefficient was also determined using hydrogenated TVA acid and was found to be 32 at 50° C. A solution of similar strength was then made from C$_9$-extractant that previously had been essentially freed of nonane-1,1,2-triphosphonic acid by extensive washing with water. The distribution coefficients at 50° C. were 2.8 and 18 respectively using untreated and hydrogenated TVA acids. This example shows that nonane-1,1,2-triphosphonic acid contributes significantly to the extractive power of the $C_9$-extractant, but that it is not an indispensable component of the extractant.

EXAMPLE 6

Uranium Extraction with Crude $C_{12}$-Extractant

A solution containing crude $C_{12}$-extractant (10 wt %), dibutyl butylphosphonate (10 wt %) and kerosene (80 wt %) was used to extract uranium from untreated 8.13 M TVA acid at 50° C. The distribution coefficient for uranium extraction was about 2. The same solution was used to extract uranium from 10.5 M phosphoric acid produced by Nissan Chemical Industries (Japan) using the hemihydrate process. The acid had been treated with carbon black (1 g per 100 mL) and filtered before the extraction but had not been submitted to any reductive treatment. The distribution coefficient for uranium extraction was 1.5 at 60° C. and 1.2 at 70° C.

COMPARATIVE EXAMPLE 7

Attempted Stripping with $HF/H_2SO_4$

A 5.2 mL aliquot of a 20 wt % chloroform solution of crude $C_9$-extractant was shaken with 100 mL of 5.5 M reagent grade phosphoric acid containing 31.5 mg dissolved U(IV). After extraction, the aqueous layer contained 0.90 mg U(IV). The organic extract was stirred for 17 h at room temperature with 5.2 mL of an aqueous solution containing 25% $H_2SO_4$ and 20% HF. Analysis of the aqueous layer revealed that only 0.43 mg uranium had been stripped from the organic extract.

EXAMPLE 8

Uranium Extraction with Crude $C_{12}$ Extractant Prepared at 110° C.

The reaction product of lauric acid with phosphorous trichloride and water at 50° C. then at 110° C. for 16 hours was worked up by addition of water and evaporation of volatiles. An extractant solution was made by dissolving the crude residue (10 wt. %) in DBBP (10 wt. %) and kerosene (80%). This solution was used to extract uranium from untreated 8.1 M TVA acid at 50° C. and a distribution coefficient of 2.1 was obtained.

EXAMPLE 9

Uranium Extraction with $C_{13}$ Extractant/Xylene

The crude reaction product of iso-tridecanoic acid with $PCl_3$ and water at 50° C. then at 150° C. for 16 hours, was dissolved in xylene to make a 10% solution. This solution was used to extract uranium from 8.1 M TVA acid and a distribution coefficient of 4.3 was obtained.

What is claimed is:

1. A process of recovering uranium values from an aqueous phosphoric acid solution by extracting the uranium values from the aqueous phosphoric acid solution with an organic solution containing an organophosphorus extractant and stripping the uranium values from the organic solution wherein the improvement comprises:
    (a) contacting the aqueous phosphoric acid solution with an organic solution of a mixture of organophosphorus compounds containing a 1-hydroxy-1,1-alkanediphosphonic acid of 8–18 carbons in a hydrocarbon solvent and a substantially water-insoluble cosolvent at a temperature between about 50° C. and about 70° C. to extract uranium values into the organic solution,
    (b) contacting the organic solution containing uranium values with an aqueous hydrogen fluoride solution of between about 30 and about 70 weight percent hydrogen fluoride, and
    (c) recovering the uranium values as a precipitate.
2. The process of claim 1 wherein said 1-hydroxy-1,1-alkanediphosphonic acid contains 9–15 carbons.
3. The process of claim 2 wherein said 1-hydroxy-1,1-alkanediphosphonic acid is 1-hydroxy-1,1-nonanediphosphonic acid.
4. The process of claim 2 wherein said 1-hydroxy-1,1-alkanediphosphonic acid is 1-hydroxy-1,1-dodecanediphosphonic acid.
5. The process of claim 1 wherein said mixture of organophosphorus compounds is dissolved in kerosene and a trialkylvphosphate cosolvent or dialkyl alkylphosphonate cosolvent.
6. The process of claim 1 wherein said mixture of organophosphorus compounds is between about 5 and about 25 weight percent of said organic solution.
7. The process of claim 6 wherein said aqueous phosphoric acid solution is contacted with organic solution at a volume ratio of acid solution to organic solution between about 10:1 and about 1:5.
8. The process of claim 1 wherein said phosphoric acid solution is between about 5 and about 15 molar.
9. The process of claim 8 wherein said phosphoric acid solution is between about 8 and about 11 molar.
10. A process of recovery uranium values from an aqueous phosphoric acid solution by extracting the uranium values from the aqueous phosphoric acid solution with an organic solution containing an organophosphorus extractant and stripping the uranium values from the organic solution wherein the improvement comprises:
    (a) contacting the aqueous phosphoric acid solution at a temperature between about 50° C. and about 70° C. with an organic solution of a hydrocarbon solvent, a substantially water insoluble cosolvent and a mixture of organophosphorus compounds formed by a method of reacting a carboxylic acid of 8–18 carbons with $PCl_3$ in the presence of water or by a method of reacting the corresponding acid chloride or anhydride with phosphorous acid to extract uranium values into the organic solution,
    (b) contacting the organic solution containing uranium values with an aqueous hydrogen fluoride solution of between about 30 and about 70 weight percent hydrogen fluoride, and
    (c) recovering the uranium values as a precipitate.
11. The process of claim 10 wherein said mixture of organophosphorus compounds is between about 5 and about 25 weight percent of said organic solution.
12. The process of claim 11 wherein said aqueous phosphoric acid solution is contacted with organic solution at a volume ratio of acid solution to organic solution between about 10:1 and about 1:5.
13. The process of claim 10 wherein said phosphoric acid solution is between about 5 and about 15 molar.
14. The process of claim 13 wherein said phosphoric acid solution is between about 8 and about 11 molar.
15. The process of claim 10 wherein said mixture of organophosphorus compounds is produced by the reaction of a carboxylic acid of the formula R-COOH with PCl$_3$ in the presence of water, with R being alkyl of 7–17 carbons.

16. The process of claim 15 wherein R is alkyl of 8–14 carbons.

17. The process of claim 16 wherein R is octyl.

18. The process of claim 16 where R is undecyl.

19. A process of recovering uranium values from an aqueous phosphoric acid solution by extracting the uranium values from the aqueous phosphoric acid solution with an organic solution containing an organophosphorus extractant and stripping the uranium values from the organic solution wherein the improvement comprises:

(a) contacting the aqueous phosphoric acid solution with an organic solution of a mixture of organophosphorus compounds containing an alkane-1,1,2-triphosphonic acid of 8–18 carbons to extract uranium values into the organic solution, (b) contacting the organic solution containing uranium values with an aqueous hydrogen fluoride solution of between about 30 and about 70 weight percent hydrogen fluoride, and (c) recovering the uranium values as a precipitate.

20. The process of claim 19 wherein said alkane-1,1,2-triphosphonic acid is of 9–15 carbons.

21. The process of claim 20 wherein said alkane-1,1,2-triphosphonic acid is nonane-1,1,2-triphosphonic acid.

22. The process of claim 20 wherein said alkane-1, alkane-1,1,2-triphosphonic acid is dodecane-1,1,2-triphosphonic acid.

23. The process of claim 19 or 20 wherein said mixture of organophosphorus compounds is dissolved in a hydrocarbon solvent and a substantially water-insoluble cosolvent.

24. The process of claim 23 wherein said mixture of organophosphorus compounds is dissolved in kerosene and a trialkylphosphate solvent or dialkyl alkylphosphonate cosolvent.

25. The process of claim 19 or 20 wherein the aqueous phosphoric acid solution is contacted with the organic solution at a temperature of between about 0° C. and about 75° C.

26. The process of claim 25 wherein said temperature is between about 50° C. and about 70° C.

27. The process of claim 26 wherein said phosphonic acid solution is between about 8 and about 11 molar.

* * * * *